United States Patent [19]
Stirbl et al.

[11] Patent Number: 5,507,291
[45] Date of Patent: Apr. 16, 1996

[54] METHOD AND AN ASSOCIATED APPARATUS FOR REMOTELY DETERMINING INFORMATION AS TO PERSON'S EMOTIONAL STATE

[76] Inventors: Robert C. Stirbl, 247 Wadsworth Ave., New York, N.Y. 10033; Peter J. Wilk, 185 W. End Ave., New York, N.Y. 10023

[21] Appl. No.: 222,835

[22] Filed: Apr. 5, 1994

[51] Int. Cl.$^6$ ............................................. A61B 5/04
[52] U.S. Cl. ........................... 128/653.1; 128/661.08; 128/691; 128/745; 128/660.02
[58] Field of Search ................ 128/653.1, 660.01, 128/660.02, 661.08, 691, 736, 745, 664

[56] References Cited

U.S. PATENT DOCUMENTS

| | | | |
|---|---|---|---|
| 3,483,860 | 12/1969 | Namerow | 128/653.1 |
| 3,598,107 | 8/1971 | Ishikawa et al. | 128/653.1 |
| 3,875,929 | 4/1975 | Grant | 128/653.1 |
| 3,951,134 | 4/1976 | Malech | 128/653.1 |
| 3,993,995 | 11/1976 | Kaplan et al. | 128/653.1 |
| 4,048,986 | 9/1977 | Ott | 128/653.1 |
| 4,085,740 | 4/1978 | Allen, Jr. | 128/653.1 |
| 4,365,637 | 12/1982 | Johnson | 128/734 |
| 4,509,531 | 4/1985 | Ward | 128/736 |
| 4,556,057 | 12/1985 | Hiruma et al. | |
| 4,569,354 | 2/1986 | Shapiro et al. | |
| 4,981,139 | 1/1991 | Pfohl | |
| 4,991,585 | 2/1991 | Mawhinney | 128/653.1 |
| 4,998,533 | 3/1991 | Winkelman | 128/653.1 |
| 5,022,405 | 6/1991 | Hök et al. | |
| 5,099,852 | 3/1992 | Meister et al. | 128/691 |
| 5,137,027 | 8/1992 | Rosenfeld | 128/745 |
| 5,305,748 | 4/1994 | Wilk | |
| 5,360,005 | 11/1994 | Wilk | 128/653.1 |

*Primary Examiner*—Krista M. Zele
*Attorney, Agent, or Firm*—R. Neil Sudol; Henry D. Coleman

[57] ABSTRACT

In a method for remotely determining information relating to a person's emotional state, an waveform energy having a predetermined frequency and a predetermined intensity is generated and wirelessly transmitted towards a remotely located subject. Waveform energy emitted from the subject is detected and automatically analyzed to derive information relating to the individual's emotional state. Physiological or physical parameters of blood pressure, pulse rate, pupil size, respiration rate and perspiration level are measured and compared with reference values to provide information utilizable in evaluating interviewee's responses or possibly criminal intent in security sensitive areas.

33 Claims, 4 Drawing Sheets

METHOD AND AN ASSOCIATED APPARATUS FOR REMOTELY DETERMINING INFORMATION AS TO PERSON'S EMOTIONAL STATE

BACKGROUND OF THE INVENTION

This invention relates to a method and an associated apparatus for remotely determining information pertaining to an individual's emotional and/or metabolic state.

In many situations, to make decisions it would be helpful to have objective information regarding a person's emotional state. Such information is useful in ascertaining the person's thoughts and intentions. For example, in an interview situation, objective information as to the interviewee's emotional state provides a better basis on which to judge the truthfulness of the interviewee's responses to questions. Such information has been conventionally obtained, in certain applications, by so-called lie detectors. A problem with such devices is that the interviewee is necessarily aware of the testing. This introduces a complication in evaluating the results of the lie detector testing. Accordingly, it would be desirable to provide a means for objectively determining emotional state parameters without the knowledge of the subject.

Such technology would also be useful for medical purposes, to determine, for example, whether a person is in danger of a life-threatening heart attack. Some of the physiological parameters which indicate emotional stress are also indicative of the physical stress of a heart condition. Such physiological parameters include blood pressure and pulse rate. An irregular pulse is especially indicative of a cardiac arrythmia which may be a prelude to myocardial infarction.

Technology which serves to objectively identify emotional state without the knowledge of the subject is also useful in security applications. It would be beneficial, for example, to detect an individual contemplating a robbery or hijacking prior to entry of that individual into a bank or an airplane.

OBJECTS OF THE INVENTION

An object of the present invention is to provide a method for obtaining information pertinent to a person's emotional state, without the person's knowledge.

Another object of the present invention is to provide such a method for use in determining the truthfulness or sincerity of the person during an interview.

An alternative object of the present invention is to provide such a method for use in checking the health of the person.

Another alternative object of the present invention is to provide such a method for use in detecting those contemplating a criminal act.

Another, more particular, object of the present invention is to provide such a method which is implemented remotely, without touching the subject.

Yet another object of the present invention is to provide an associated apparatus or system for obtaining information pertinent to a person's emotional state, without the person's knowledge.

These and other objects of the present invention will be apparent from the drawings and detailed descriptions herein.

SUMMARY OF THE INVENTION

A method for remotely determining information relating to a person's emotional state, comprising the steps of (a) generating waveform energy having a predetermined frequency and a predetermined intensity, the step of generating being implemented at a location remotely spaced from a target individual, (b) wirelessly transmitting the waveform energy towards the individual, (c) detecting energy emitted or reflected from the individual in response to the waveform energy, and (d) automatically analyzing the emitted or reflected energy to derive information relating to the individual's emotional state.

According to another feature of the present invention, the step of analyzing includes the steps of determining a value related to a physiological parameter taken from the group consisting of blood pressure, pulse rate, respiration rate, pupil size, and perspiration, and comparing the value with a stored reference value to identify a change in the parameter.

Where the parameter is respiration rate and the detected energy is reflected from the individual's chest wall, the method further comprises the steps of processing the reflected energy to determine location of the individual's chest wall, and automatically monitoring the individual's position and compensating for changes in the individual's position in determining changes in location of the individual's chest wall.

Alternatively, respiration rate may be determined by monitoring the differential remote absorption of the individual subject's exhalation gases. Invisible electromagnetic radiation from a source such as a light emitting diode (e.g., a laser diode) is directed towards the subject's mouth. The diode generated radiation is modulated at a high rate with a phase-locked component. Radiation returning from the subject and particularly from gases at the subject's mouth are filtered via an electro-optical modulating polarization component. This polarization component may take the form of a filter wheel rotating, for example, at a speed between 300 and 1,000 Hz. An opto-electric detector senses the radiation penetrating the filter wheel. An amplifier phase-locked with the modulator component serves to detect signals only at the frequency of modulation. Any ambient constant energy which is not part of the measuring signal is filtered out.

In remotely monitoring a person's respiration rate, the waveform energy may be modulated electromagnetic radiation or ultrasonic or subsonic pressure waves. Where the measuring waveform is electromagnetic, the measurement may be effectuated using the principles of differential backscatter absorption or interferometery to detect phase changes owing to a change in position of the subject surface (the individual's chest wall). The wavelength or frequency of the modulated electromagnetic radiation is selected from the infrared and near-millimeter portions of the spectrum so as to penetrate clothing material and be reflected from the underlying skin surface. Where the measuring waveform is an ultrasonic or subsonic pressure wave, changes in position of the chest wall may be detected via phase changes and/or by changes in travel time.

Where the monitored parameter is pulse rate, the measuring energy may be modulated electromagnetic radiation, in the near-ultraviolet, infrared or near-millimeter ranges. A collimated beam of radiation is generated and directed or aimed towards a predetermined point on the individual overlying or on a blood vessel. The emitted or reflected energy is processed to determine (1) intensity, change in intensity or change in polarization or fluorescence of the emitted or reflected energy and (2) amount of transdermal absorption. Changes in transdermal absorption can be tracked to determine changes in volume of blood and, accordingly, the pulse of the target individual. If necessary, variance in the emitted or reflected radiation due to surface moisture (perspiration) can be compensated for by automatically measuring emitted or reflected radiation at an additional point proximate to the predetermined point to determine a level of surface moisture. Any differential owing to varying surface moisture can be isolated and removed or used as an indication of metabolic activity or emotional state.

The surface moisture is detected by measuring the intensity of the radiation returning to a detector from a selected point on the skin surface of the target individual. Surface moisture is indicative of stress, as is known by galvanic skin response, the electrical measure which forms the basis for conventional lie detection.

It is to be noted that some measurements made in accordance with the present invention can be improved by taking into account movements of the subject. For example, where pulse rate is measured by monitoring changes in transdermal radiation absorption, the individual's position can be automatically monitored. Thus, the radiation beam's direction can be adjusted to track the target blood vessel. The individual's position and configuration (posture) can be tracked by a simple pattern recognition program analyzing input from a camera (e.g., charge coupled device).

Where the parameter is blood pressure, the measuring medium may be ultrasonic or subsonic pressure waves. An incoming ultrasonic or subsonic pressure wave which has been reflected from a blood vessel below the skin surface of the subject (e.g., at the temple or in the retina) is monitored to determine the instantaneous blood flow rate or velocity. The principles of this measurement procedure are known from conventional ultrasonic Doppler devices. These devices are generally placed in contact with a patient or inserted into the body and only determine blood flow rate. In accordance with the present invention, ultrasonic measurements of blood flow rate are implemented remotely, i.e., the ultrasonic wave generator and the detector are spaced by at least several feet from the individual subject. In addition, in analyzing the incoming ultrasonic waves, a blood pressure parameter is automatically calculated using Bernoulli's equation.

An alternative technique for measuring blood pressure utilizes Doppler speckle interferometery. The speed of the measurement pulses are matched to the average speed of the blood so that there is a modulation in the self interference term of the emitted or reflected light and the reference light. Basically, this is a kind of temporal interferometry.

Where the monitored parameter is pupil size, detection may be implemented by counting pixel receptors of a camera corresponding to the subject's pupil. In this case, the measuring energy is electromagnetic (infrared, near-millimeter).

Generally, a monitored physiological or emotional-state parameter is compared with a reference value which includes a previously measured value for the parameter. For example, the pressure value obtained through calculations based on blood vessel flow rate is compared with previous blood pressure values computed seconds or minutes before by the same technique. An average value for the pressure parameter may be computed and used to detect rises or falls in blood pressure possibly indicative of emotional stress. Such emotional stress may be connected with prevarication, with criminal intent, or with a cardiovascular malfunction. Where people entering a bank or airplane, for example, are being monitored, the blood pressure parameter must be correlated with other measured parameters, such as pulse rate and respiration rate, and with average ranges for those parameters, based on age, size and sex.

Similarly, the pulse rate may be measured and compared with prior pulse rates of the individual test subject or with an average pulse rate for people of the same age, sex and size. These prior values of the monitored parameter or of average ranges are stored in encoded form in a memory.

Changes in any physiological or physical parameter measured or monitored as described herein can be used at least as indicators or alert signals that an emotional state exists or has come into being in the targeted individual. Where the individual is an interviewee, the parametric changes may be correlated with the subjects of the conversation with the interviewee. This correlation may be executed subsequently to the interview, where the interview is recorded on audio and/or video tape.

Where the waveform energy is collimated modulated electromagnetic radiation, the step of generating includes the steps of producing an electromagnetic waveform of the predetermined frequency and collimating the electromagnetic waveform. Then the step of transmitting includes the step of directing the waveform to a predetermined point on the individual. This target point may overlie a preselected blood vessel (pulse rate, blood pressure). Alternatively, it may lie in the retina or carotid artery of the targeted individual or test subject (pulse rate, blood pressure). It may be the subject's chest wall (respiration rate). In the case of perspiration rate, the target point is preferably a point having a characteristically high number of sweat glands.

According to another feature of the present invention, the directing of the collimated beam of (modulated) electromagnetic radiation includes the steps of monitoring the location of the individual. Thus, the direction of the beam is controlled to take into account the individual's voluntary and involuntary movements so that the selected target point is effectively tracked.

This monitoring of the individual's position and configuration may be implemented via video processing technology, for example, by deriving a contour of the individual and comparing the contour with previously determined generic contour data. Such technology is similar to that used in so-called "smart bombs" in military applications.

According to an additional feature of the present invention, the step of analyzing the incoming emitted or reflected waveform energy includes the step of measuring the emitted or reflected energy to determine at least one parameter selected from the group including frequency, fluorescence, amplitude or intensity, change in intensity, change in phase, and change in polarization. The step of analyzing also includes the step of automatically comparing the determined parameter with a reference value, which may incorporate at least one prior measurement of the selected parameter with respect to the individual.

Pursuant to another feature of the present invention, the methodology further comprises the step of changing a frequency of the waveform during a sequence of successive measurements.

A system for remotely determining information relating to a person's emotional state comprises, in accordance with the present invention, a waveform generator for generating waveform energy having a predetermined frequency and a predetermined intensity, the generator being remotely spaced from a target individual. A transmitter is operatively connected to the waveform generator for wirelessly transmitting the waveform energy towards the individual. A detector is provided for detecting energy emitted or reflected from the individual in response to the waveform energy. A processor is operatively connected to the detector for analyzing the emitted or reflected energy to derive information relating to the individual's emotional state. The processor is also operatively connected to at least one of the waveform generator and the transmitter for controlling emission of energy towards the individual. The processor is thus able to correlate the incoming energy with that transmitted towards the targeted individual.

In accordance with another feature of the present invention, the processor includes first componentry for determining a value related to a monitored physiological or physical parameter taken from the group consisting of blood pressure, pulse rate, respiration rate, pupil size, skin fluorescence, and perspiration. The processor further includes second componentry operatively connected to the first componentry for comparing the determined value with a stored reference value to identify a change in the parameter.

Where the monitored parameter is respiration rate, the transmitter is controlled in one particular embodiment by the processor to direct the measuring energy towards the individual's chest wall. The first componentry of the processor includes means for processing the emitted or reflected energy to determine location of the individual's chest wall and means for automatically monitoring the individual's position and compensating for changes in the individual's position in determining changes in location of the individual's chest wall. In measuring respiration rate, the measuring waveform energy is modulated electromagnetic radiation or ultrasonic or subsonic pressure waves. The waveform generator includes either an electromagnetic energy generator or an electro-acoustic transducer for producing ultrasonic or subsonic pressure waves.

Where the monitored parameter is pulse rate, the waveform energy is modulated electromagnetic radiation, in the near-ultraviolet, infrared or near-millimeter ranges and the transmitter is controlled by the processor to direct the waveform energy towards a predetermined point on the individual overlying or on a blood vessel. The first processing componentry of the processor then includes means for deriving (1) intensity of the emitted or reflected energy and (2) amount of transdermal absorption. In addition, the processor may include structure and/or programming for automatically measuring emitted or reflected radiation at an additional point proximate to the predetermined point to determine a level of surface moisture (e.g., perspiration) and means for compensating for surface absorption due to surface moisture in determining the amount of transdermal absorption.

In accordance with another feature of the present invention, the system further comprises tracking circuitry operatively connected to the processor for automatically and remotely monitoring the individual's position, thereby enabling the processor to track changes in position of the predetermined point from which measurements are remotely taken.

Where the monitored parameter is blood pressure, the waveform energy takes the form of an ultrasonic or subsonic pressure wave. The processor then includes architecture and programming for processing a reflected, incoming ultrasonic or subsonic pressure wave to derive a rate of blood flow in a preselected blood vessel of the individual. The processor also includes means for automatically calculating a blood pressure parameter from the derived blood flow rate. In analyzing the incoming ultrasonic or subsonic waves, the processor automatically calculates a blood pressure parameter using Bernoulli's equation or Doppler speckle interferometry. In the latter case, the speed of the measurement pulses are matched to the average speed of the blood so that there is a modulation in the self interference term of the emitted or reflected light and the reference light. Basically, this is a kind of temporal interferometry.

Where the monitored parameter is pupil size and the waveform energy is electromagnetic radiation, the detector includes pixel receptors of a camera. The processor includes means for automatically counting pixels corresponding to a diameter of the individual's pupil.

Generally, the processor compares a monitored physiological or emotional-state parameter with a reference value which includes a previously measured value for the parameter. The reference value is stored in a memory of the processor. A pressure value obtained through calculations based on blood vessel flow rate is compared with previous blood pressure values computed and stored by the processor during the same testing or measurement session. The processor may compute an average value for the pressure parameter and use the average value to detect rises or falls in blood pressure possibly indicative of emotional stress.

Where the parameter is perspiration, the waveform energy is modulated electromagnetic radiation and the detector includes means for measuring a change in polarization or intensity at the incident or fluorescent wavelength of the radiation emitted or reflected from a predetermined point on the individual. Generally the amount emitted or reflected will vary as a function of the amount of perspiration on the skin surface.

Where the waveform energy is collimated modulated electromagnetic radiation, the waveform generator includes a source for producing an electromagnetic waveform of the predetermined frequency and elements for collimating the electromagnetic waveform. The transmitter includes components (e.g., lens, directional antennae, mechanical drives) for directing the waveform to a predetermined point on the individual.

In accordance with a further feature of the present invention, the system also comprises a monitoring unit operatively connected to the processor for monitoring the location of the individual, the monitoring unit being operatively connected to the directional components of the transmitter for controlling the operation thereof. The location monitoring unit may include means for deriving a contour of the individual and means connected thereto for comparing the contour with previously determined generic contour data. More specifically, the position and configuration of the target may be tracked by processing video input from a camera such as a charge coupled device. The techniques of pattern recognition may be utilized to track changes in location of a selected target point as the individual subject moves during the course of the testing period. Ultrasonic or subsonic waves may also be used to determine the position of the individual subject.

In an actual application of the instant invention, the transmitter and detector may be located in a wall of a room and camouflaged by decorative features. Of course, multiple transmitters and detectors may be located in different locations about the subject individual. Where an individual is moving along a path, multiple transmitters and detectors may be necessary to obtain sufficient information. Input from a series of detectors are analyzed to obtain information as to emotional or physical state of the individual.

In accordance with yet another feature of the present invention, the detector includes means for measuring the emitted or reflected energy to determine at least one parameter selected from the group including frequency, fluorescence, amplitude or intensity, change in intensity, change in phase, and change in polarization, while the processor includes means for comparing the determined parameter with a previously determined reference value. As discussed above, the reference value may incorporate at least one prior measurement of the selected parameter with respect to the individual. The processor then includes means for deriving the reference value from the prior measurement.

Where the waveform energy is electromagnetic, several frequencies may be used to collect data. The different frequencies may be multiplexed or transmitted in sequence from a single transmitter or generated and transmitted simultaneously in the case of multiple transmitters. Where a single waveform generator is used, the generator includes means for changing a frequency of the waveform during a sequence of successive measurements.

A method and associated apparatus in accordance with the present invention enable information pertinent to a person's emotional state to be obtained without the person's knowledge. This information is useful in determining the truthfulness or sincerity of an interviewee. Thus, people being interviewed for sensitive job positions or in connection with a criminal investigation may be monitored to elicit information pertinent to their veracity. Of course, legal limitations may exist in using the garnished information as evidence in criminal trials.

A method and associated apparatus in accordance with the present invention are also useful for automatically checking health of individuals. A company may have the apparatus installed for checking the health of employees. Hospitals may use the invention for an additional check on patients.

A method and apparatus in accordance with the present invention can provide information useful in evaluating people entering a high security area for purposes of determining whether anybody is possibly contemplating a criminal act. Usually, people with such criminal intent will betray themselves by elevated pulse rates, increased blood pressure, heightened respiration rates, and/or excessive amounts of perspiration. In the event that one or more of these physiological/physical parameters exceed pre-established limits, an alert signal is automatically given to security personnel who can then attend to the suspected individuals. The alert signal may take the form of an indicator on a video monitor. An arrow pointing to the suspect or a circle about the suspect may be generated on the monitor. In addition, the processor or computer may provide details on the monitor, such as which physiological parameters are involved and the magnitude by which those parameters exceed the respective pre-established limits.

DETAILED DESCRIPTION

Figure 1:
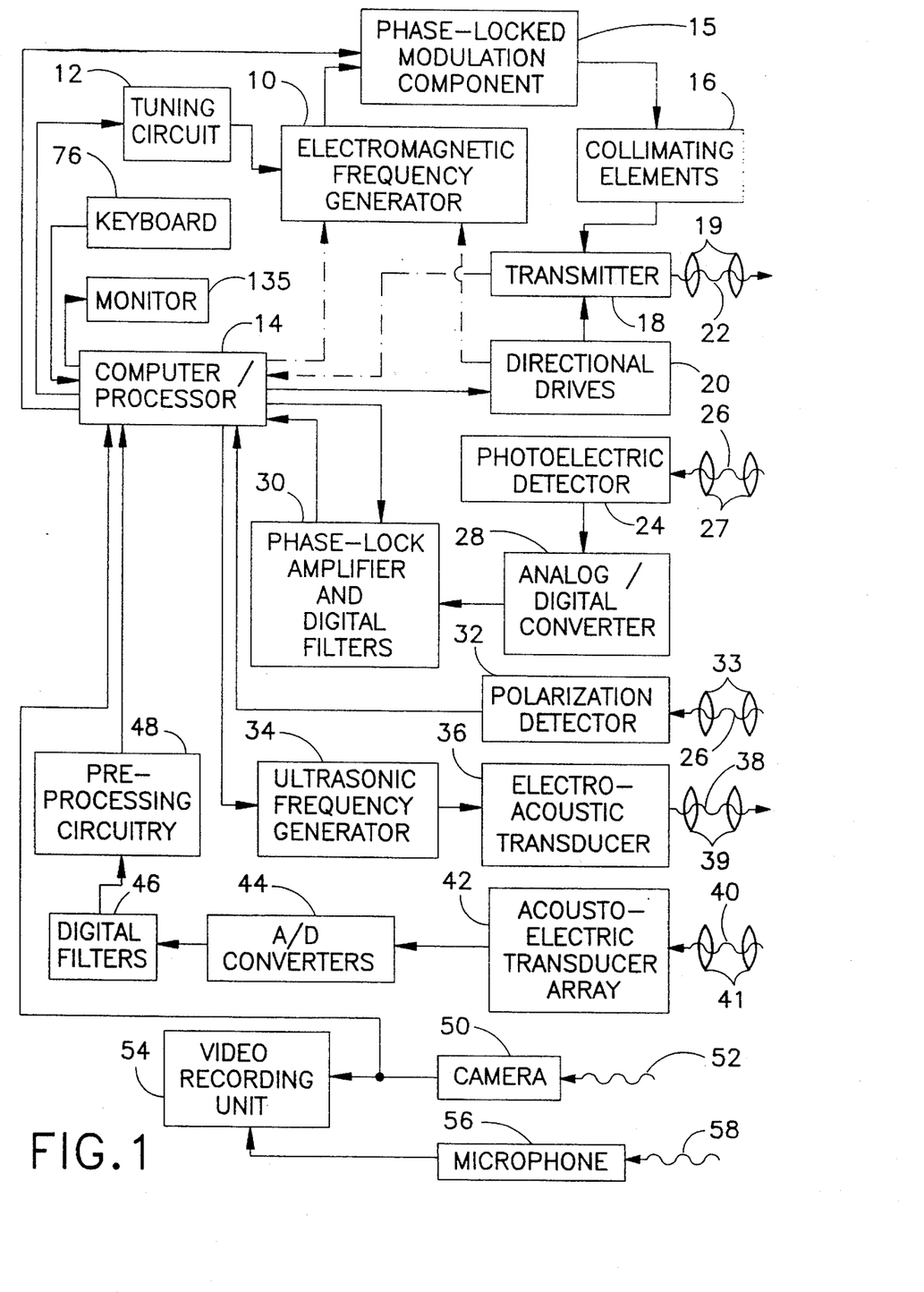
FIG. 1 is a block diagram of a system in accordance with the present invention for remotely collecting data pertaining to an individual's emotional state.

As illustrated in FIG. 1, a system for remotely determining information relating to a subject's emotional state comprises a waveform generator or source 10 for generating electromagnetic waveform energy having a predetermined frequency and a predetermined intensity. Waveform generator 10, as all the other components of the system described herein, is remotely spaced from a target individual or subject (see FIGS. 3 and 4). The frequency of the waveform energy produced by generator 10 may be adjusted within limits by a tuning circuit 12 in response to control signals from a signal processing unit in the form of a computer 14. The intensity or amplitude of an electromagnetic waveform produced by generator 10 may be varied by the generator pursuant to signals from computer 14.

Connected to generator 10 is a phase-locked modulation component 15 which provides the waveform from generator 10 with an information component which facilitates filtering of extraneous ambient waveform energy. The modulation provides a signature which facilitates detection of radiation reflected from or emitted or reflected by the individual subject in response to the testing energy produced by generator 10.

A collimating lens or other elements 16 are provided downstream of generator 10 and modulation component 15. Further downstream is a transmitter 18. Transmitter 18 may take the form of an antenna or may simply be an aperture at an output side of collimating elements 16. Focusing elements 19 may be provided about transmitter 18 for focusing the measuring radiation at a predetermined target point on the individual subject. Focusing elements 19 may be controlled by computer 14 to adjust the target point.

Computer 14 is connected at an output to a drive assembly 20 which is operatively coupled to one or more of the energy producing components, i.e., generator 10, collimating elements 16 and/or transmitter 18, for controlling the direction of an output radiation beam 22. As discussed below, computer 14 controls the direction of transmission of parameter monitoring or measuring radiation to ensure that the radiation falls on a selected target point on the individual subject, whether the individual is still or moving, and whether the target point itself varies.

As further illustrated in FIG. 1, a detector 24 in the form of a photoelectric cell is provided for detecting incoming electromagnetic energy 26 emitted or reflected from the individual subject in response to output radiation beam 22. On an input side of detector 24 is a telescoping component 27 for limiting the field of view or to a predetermined area of the individual subject under observation. At an output of photoelectric detector 24 are connected an analog-to-digital (A/D) converter 28 and, for noise reduction, a phase-locked amplifier with digital filters 30. Computer 14 is operatively connected to detector 24 via A/D converter 28 and amplifier/filters 30 for analyzing the incoming reflected energy 26 to derive information relating to the individual's emotional state. Because computer 14 is operatively connected to waveform generator 10 and transmitter 18, the computer is able to correlate specific parameters characteristic of incoming energy 26 with corresponding parameters of output radiation beam 22. Such parameters include amplitude or intensity and phase and possibly polarization and wavelength or frequency.

A polarization detector 32 including a polarization analyzer (not shown), an analog-to-digital converter (not shown), phase locked amplifier (not shown), and digital filters (not shown) is connected to computer 14 for providing that unit with polarization data. On an input side of detector 32 is a telescoping component 33 for limiting the field of view or to a predetermined area of the individual subject under observation. A polarization analyzer (not shown) may be disposed in front of detector 24 for providing computer 14 with data relating to change in polarization. In that event, the functions of polarization detector 32 are performed by the analyzer, detector 24, analog-to-digital converter 28, and phase locked amplifier with digital filters 30. The polarization of the output radiation beam 22 may be controlled in accordance with known techniques.

As discussed hereinafter with reference to FIG. 2, computer 14 includes componentry and/or programming for determining values related to one or more monitored physiological or physical parameters including blood pressure, pulse rate, respiration rate, pupil size, and perspiration. Computer 14 further includes componentry and/or programming for comparing the determined values with one or more stored reference values to identify changes in the monitored parameters. The parametric changes thus determined can be correlated with topics of an interview with the individual subject to provide interviewers with data concerning the veracity of the interviewee. The determined changes in monitored parameters can also be correlated with one another to determine with a selected individual is possibly entertaining criminal intent or is possibly a victim of a heart attack.

As further illustrated in FIG. 1, the system further comprises an ultrasonic or subsonic frequency generator 34 which is triggered or controlled by computer 14 and which is linked at an output to a piezoelectric electroacoustic transducer 36. Transducer 36 produces an ultrasonic or subsonic output wave 38 of a predetermined wavelength. Output wave 38 may be concentrated or focused by pressure wave modification elements 39 provided downstream of transducer 36.

An incoming ultrasonic or subsonic pressure wave 40 reflected from an individual and particularly from a selected target point on the individual is detected by a piezoelectric acousto-electric transducer array 42. A telescoping component 41 (as in a shot-gun microphone) may be provided on an input side of the individual acousto-electric transducer of array 42, for limiting the field of view of the transducers.

Electrical signals produced by transducer array 42 in response to incoming ultrasonic or subsonic pressure wave 40 are fed to analog-to-digital (A/D) converters 44. Converters 44 are operatively tied to digital filters 46 which in turn are connected at an output to preprocessing circuitry 48. Preprocessing circuitry 48 aids computer 14 in analyzing incoming ultrasonic or subsonic pressure wave 40 to isolate desired data pertaining to one or more preselected target points.

FIG. 1 also shows a video camera 50 (e.g., a charge coupled device) which converts incoming electromagnetic waves 52 to an electrical video signal fed to a video recording unit 54 and to computer 14. Generally, camera 50 is responsive to radiation in the optical portion of the spectrum. However, it is also possible for camera to be alternatively or additionally responsive to radiation in the infrared and/or microwave portions of the spectrum.

A microphone 56 for sensing acoustic-frequency pressure waves 58 is connected to video recording unit 54 for enabling the storage of voice-frequency utterances of an individual subject in tandem with or as a part of a video recording. Microphone 56 is operatively connected to computer 14 for providing that unit with data pertaining, for example, to voice-frequency utterances of the subject.

To monitor pulse rate, computer 14 controls tuning circuit 12 and generator 10 so that output radiation beam 22 has a wavelength in a suboptical range of the electromagnetic spectrum, i.e., in the infrared or near-millimeter range. Transmitter 18 is controlled by computer 14 via drive assembly 20 to direct output radiation beam 22 towards a predetermined point on the individual overlying or on a blood vessel. The blood vessel may be, for example in the temple or in the eye of the test subject.

Figure 2:
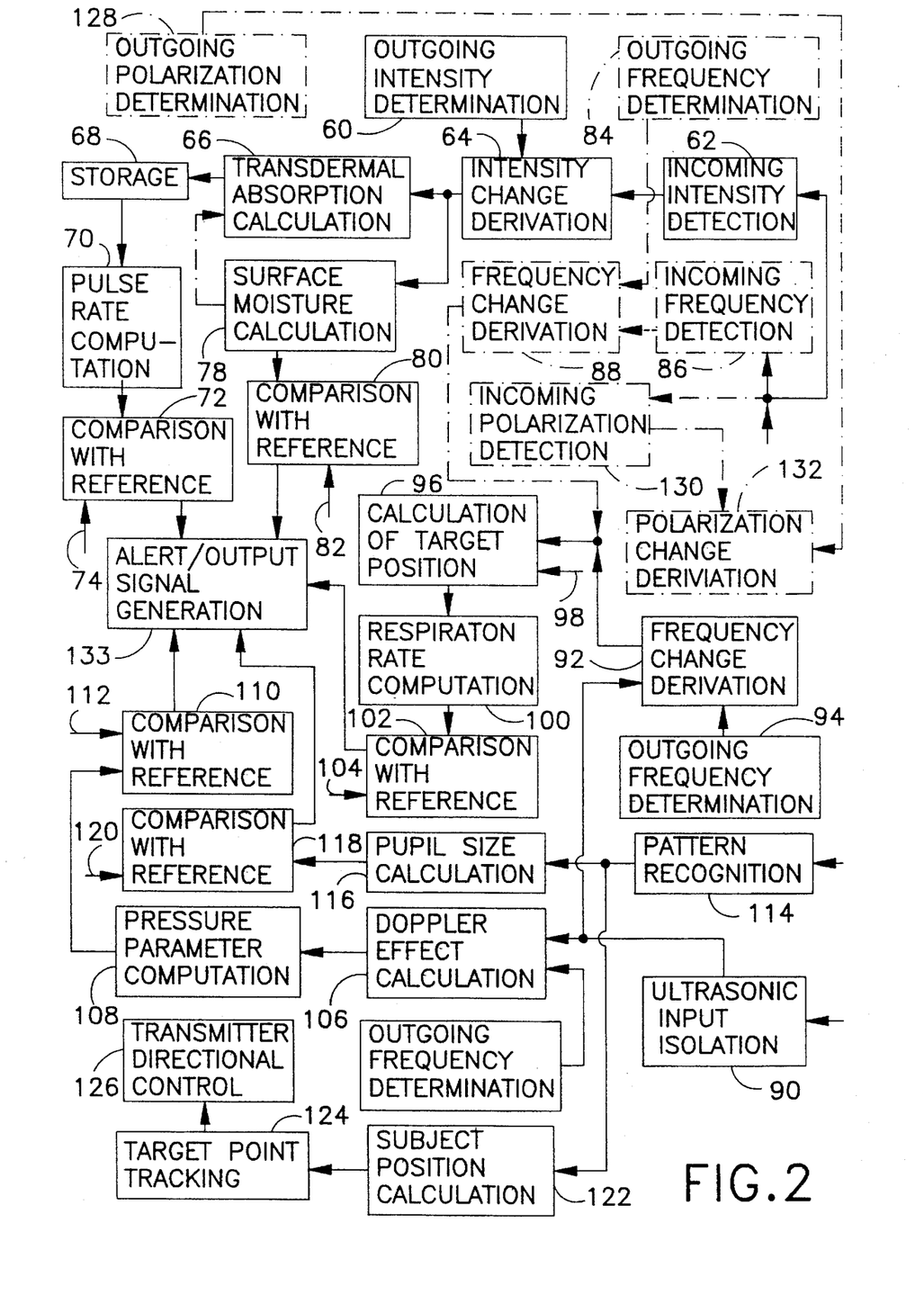
FIG. 2 is a flow-chart type diagram showing programming blocks of a computer illustrated in FIG. 1.

As illustrated in FIG. 2, for determining pulse rate, computer 14 makes a determination of the intensity or amplitude of output radiation beam 22 in a programming routine 60. In another step 62, computer 14 detects or measures the intensity of incoming reflected energy 26. In a subsequent series of steps 64 66, computer 14 derives a change in intensity between the output radiation beam 22 and the incoming reflected energy 26 and calculates a transdermal absorption value characteristic of the amount of blood in the monitored blood vessel underlying the target point on the skin surface or the retina of the individual. Each successively calculated transdermal absorption value is stored in a step 68 and used in a later computation 70 to determine a substantially instantaneous pulse rate of the individual subject.

A computed pulse rate is compared in a step 72 with a reference value (represented by input arrow 74) to ascertain information relevant to the emotional status of the person being monitored. The reference value may take the form of a previously determined average or normal pulse rate or may be calculated from a series of pulse rates of the individual during the same test session, or even during prior test sessions with the same subject. An average or normal pulse rate used as a reference value in comparison step 72 may be a function of various physical characteristics of the individual test subject, such as age and weight, and immediate history, such the exercise status. If the individual is walking, the average pulse rate will be higher than if the individual has been sitting for several minutes. The different average pulse rate values, as well as parameters pertaining to the age, weight and history of the individual test subject, may be fed to computer 14 via a keyboard 76 (FIG. 1).

In determining transdermal radiation absorption incident to computing the pulse rate of the individual test subject, computer 14 may compensate for changes in surface moisture (perspiration). Surface moisture is measured, as discussed immediately below, at a point adjacent to the pulse rate target point, but not overlying a blood vessel. Computer 14 controls drive assembly 20 to adjust the location of the target point.

As further illustrated in FIG. 2, computer 10 includes programming or hard-wired componentry for making a surface moisture calculation 78 indicative of perspiration rate. A change in intensity between the output radiation beam 22 and the incoming reflected energy 26, derived at 64, is used in calculation 78. The results of surface moisture calculation 78 are compared in a step 80 with a reference value 82. Reference value 82 may be a predetermined value characteristic, for example, of an average reflectivity of dry skin. This value is provided to computer 14 via keyboard 76. Alternatively, reference value 82 may be determined on the basis of a series of calibrating calculations of the surface moisture of the individual test subject, at the test or target point along or at a plurality of spaced points on the skin of the individual subject.

Pulse rate may alternatively be measured via a change in phase or a frequency change (Doppler) measurement. Generally, such information is obtained through ultrasonic or subsonic pressure waves, as discussed in detail hereinafter. However, the potential for obtaining such information via an electromagnetic measuring radiation is contemplated. To that end, computer 14 makes a determination 84 of the outgoing frequency of output radiation beam 22 and detects at 86 the frequency of incoming reflected energy 26. In a step 88, computer 14 derives a frequency change indicative of the velocity of a moving surface, e.g., a wall of a blood vessel in the retina of the individual test subject. A succession of velocities may be integrated to derive position values. (See steps 96, 100, and 102, discussed below).

To monitor respiration rate, computer 14 energizes frequency generator 34 and transducer 36 to emit an ultrasonic or subsonic pressure wave of a known wavelength towards the individual test subject and particularly towards the chest wall of the individual subject. As depicted in FIG. 2, computer 14 uses input from preprocessing circuitry 48 in a step 90 to isolate ultrasonic or subsonic pressure wave data corresponding the chest wall of the individual test subject. The results of this isolation 90 are used in a step 92 to derive a frequency change of ultrasonic or subsonic pressure wave 40 with respect to ultrasonic or subsonic output wave 38 (frequency determined at 94). In a step 96, computer 14 uses the frequency change data to determine position of the chest wall via an integration technique taking into account previously computed positional data at 98. In a further computation 100, computer 14 determines respiration rate. The computed respiration rate is compared in a step 102 with a reference value 104 to derive information pertinent to the contemporaneous or real-time emotional state of the individual test subject. Reference value 104 may be an average respiration rate input into computer 14 via keyboard 76. Alternatively, reference value 104 may be determined on the basis of a series of calibrating calculations of the respiration of the individual test subject. A reference value 104 in the form of a predetermined average may vary in accordance with the immediate exercise history of the individual test subject. If the individual is walking, the reference value for the respiration rate will be higher than if the individual has been sitting for a time. In addition, the reference value may vary depending on the size and apparent athleticism of the individual. People who exercise a great deal tend to have lower respiration rates (and pulse rates) than those who do not exercise. These variables may be entered into computer 14 via keyboard 76.

Respiration rate may be similarly measured by monitoring a change in frequency of incoming reflected energy 26 with respect to output radiation beam 22. In that case, of course, computer 14 controls drives 20 to direct the output radiation beam 22 toward the chest of the individual test subject.

To obtain a measurement related to blood pressure, results of isolation step 90 are used in a step 106 to calculate a Doppler effect from fluid moving in a targeted subsurface blood vessel. In step 90, computer 14 isolates ultrasonic or subsonic data corresponding to the targeted subsurface blood vessel. The Doppler effect calcuation of step 106 produces a velocity value which is used by computer 14 to compute a pressure parameter at 108. This computation is based on Bernoulli's fluid flow equation or Doppler speckle interferometery. In the latter case, the speed of the measurement pulses are matched to the average speed of the blood so that there is a modulation in the self interference term of the emitted or reflected light and the reference light.

In a subsequent step 110, the computed pressure value is compared with a reference value (112) to determine information pertaining to the contemporaneous or real-time emotional state of the individual test subject. As discussed above with respect to the evaluation of other measured parameters, the reference value 112 for blood pressure may be an average or normalized value predetermined in accordance with known blood pressure data derived from known populations.

To determine the size of a pupil of the individual test subject, the detector is camera 50 (FIG. 1). An image from camera 50 is subjected to pattern recognition processes in a step 114 (FIG. 2) so as to identify the individual's pupil in the image. In a subsequent step 116, computer 14 calculates the individual test subject's contemporaneous or real-time pupil size effectively by counting pixel receptors of camera 50 which correspond to a diameter or area of pupil. In another step 118, the calculated pupil size is compared with a reference value 120, e.g., a predetermined average.

Results of pattern recogition processes 114 are also utilizable by computer 14 to track the location and posture of the individual test subject. In a step 122, computer 14 calculates position of the individual test subject based on the pattern recognition data from processes 114. The results of these calculations 122 are used by computer 14 in a step 124 to track the selected target point (e.g., over a blood vessel, in the retina). Computer 14 controls directional drive assembly 20 (FIG. 1) in a step 126 in accordance with the position of the target point as determined in step 124.

Pattern recognition processes 114 may include steps for deriving a contour of the individual test subject and for comparing the contour with previously determined generic contour data. The techniques of pattern recognition may be utilized to track changes in location of a selected target point as the individual subject moves during the course of the testing period. Ultrasonic or subsonic waves may also be used to determine the position of the individual subject.

It is contemplated that other information such as polarization and phase contained in an electromagnetic output radiation beam 22 and incoming reflected energy 26 may be used for remotely obtaining information pertaining to the emotional state of the individual test subject. To that end, for example, computer 14 determines the polarization (and/or phase) of output radiation beam 22 at 128 and of incoming reflected energy 26 at 130. A polarization change is derived in step 132.

Another source of remotely obtainable data about the emotional and/or metabolic state of a subject is skin fluorescence. An activating or stimulus wavelength in the ultraviolet range is produced by generator 10 and directed from transmitter 18 towards a predetermined target spot on the individual subject. The target spot is scanned by photoelectric detector 24 to determine the fluorescent output of the target spot. A filter wheel (not shown) may be provided at the input of detector 24 for facilitating determination of the wavelength of fluorescent energy.

If in one or more of the comparison steps 72, 80, 102, 110, 118, computer 14 determines that the respective computed value for the blood pressure, perspiration rate, respiration rate, blood pressure and/or pupil size has exceeded or fallen below the respective reference value, the computer issues an alert signal in a step 133. That alert signal may take a visually perceptible form. For example, computer 14 may generate a message on a monitor 135 (FIG. 1). The message may include particulars as to the detected anomaly in the monitored physiological signs of the individual under observation. The identity of the anomalous parameters, as well as the kind and amount of deviation may be displayed on monitor 135.

Figure 3:
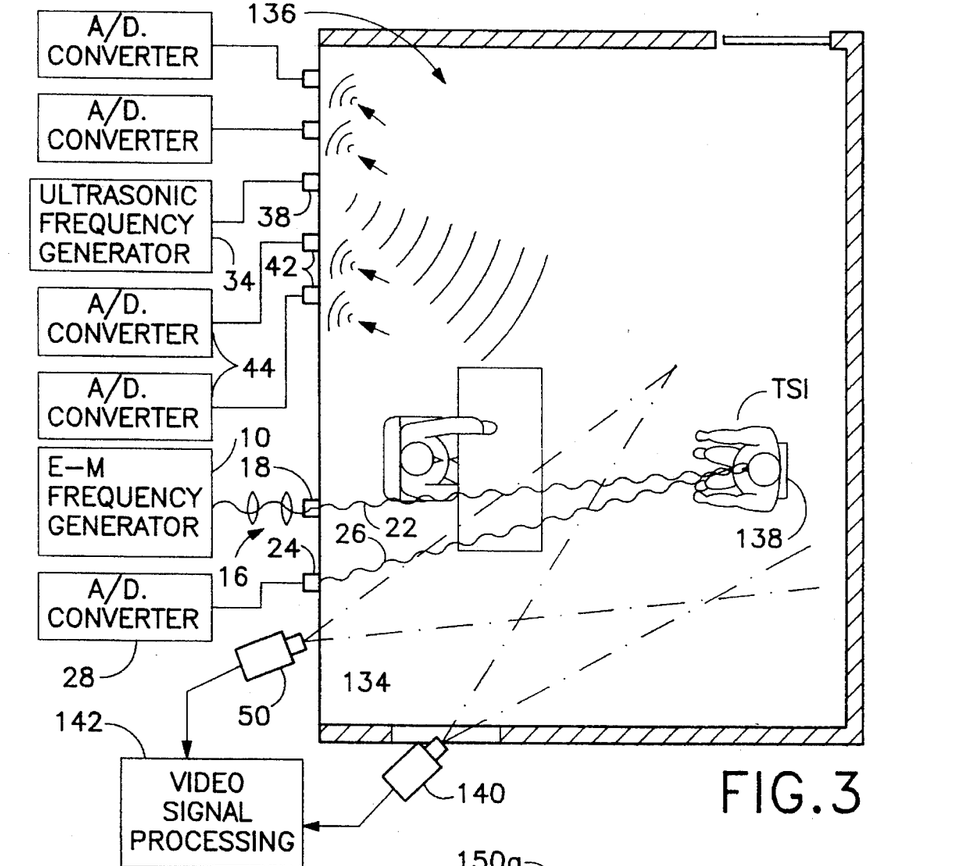
FIG. 3 is partially a block diagram and partially a schematic plan view showing a particular use of the system of the present invention.

As depicted in FIG. 3, in an actual application of the system of FIGS. 1 and 2, transmitter 18 and photoelectric detector 24 are located in a wall 134 of a room 136 and camouflaged by decorative features such as wall sculptures or paintings (not shown). FIG. 3 only shows some of the componentry of the system of FIG. 1, for purposes of simplicity. An individual test subject TSI is seated in a chair 138 in room 126. Camera 50 is one of a pair of cameras 50 and 140, which are connected to a video processing circuit 142 (e.g., computer 14). The dual input facilitates triangulation of the position of individual test subject TSI in room 136.

Figure 4:
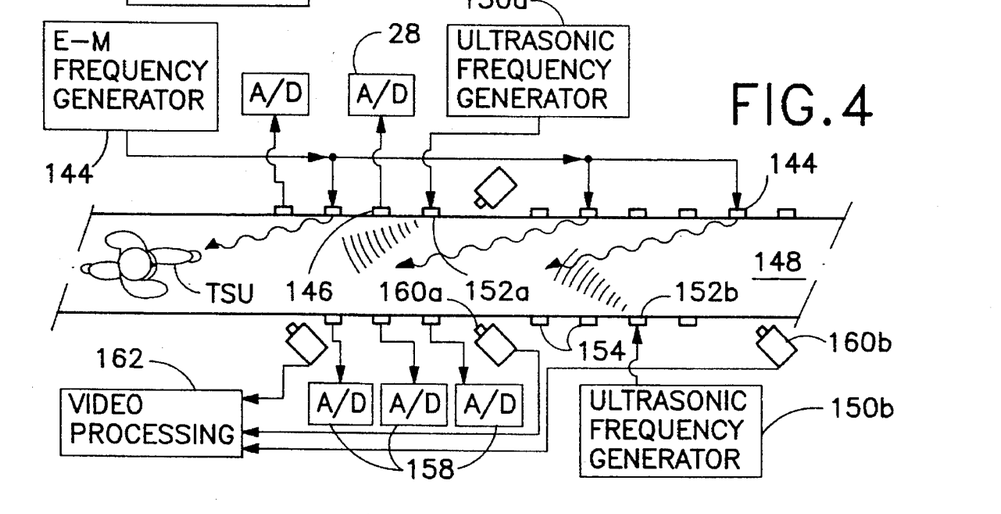
FIG. 4 is partially a block diagram and partially a schematic plan view showing a another particular use of the system of the present invention.

FIG. 4 shows multiple electromagnetic radiation transmitters 144 and multiple photoelectric detectors 146 spaced from one another along a path 148 followed by a selected individual test subject TSU. Input from detectors 146 are analyzed to obtain information as to emotional or physical state of the individual TSU. The modified system of FIG. 4 also includes multiple ultrasonic or subsonic frequency generators 150a, 150b connected to respective piezoelectric transducers 152a, 152b. Generators 150a and 150b generally produce pressure waves of different wavelengths or frequencies to facilitate differentiation and processing of ultrasonic or subsonic input at spaced points along path 148. A single array of piezoelectric acousto-electric transducers 154 may be used to detect the ultrasonic or subsonic signals from individual test subject TSU. Transducers 154 are connected to A/D converters 158. The system of FIG. 4 also includes multiple video cameras 160a, 160b spaced along path 148. A video processing unit 162 receives signals from cameras 160a, 160b. The signals from cameras 160a, 160b are used as discussed above to determine pupil size and subject location.

With respect to the system of FIG. 1, computer 14 may be programmed to control tuning circuit 12 so that generator 10 produces different frequencies in an interdigitated or multiplexed pattern for augmenting the obtainable information.

Figure 5:
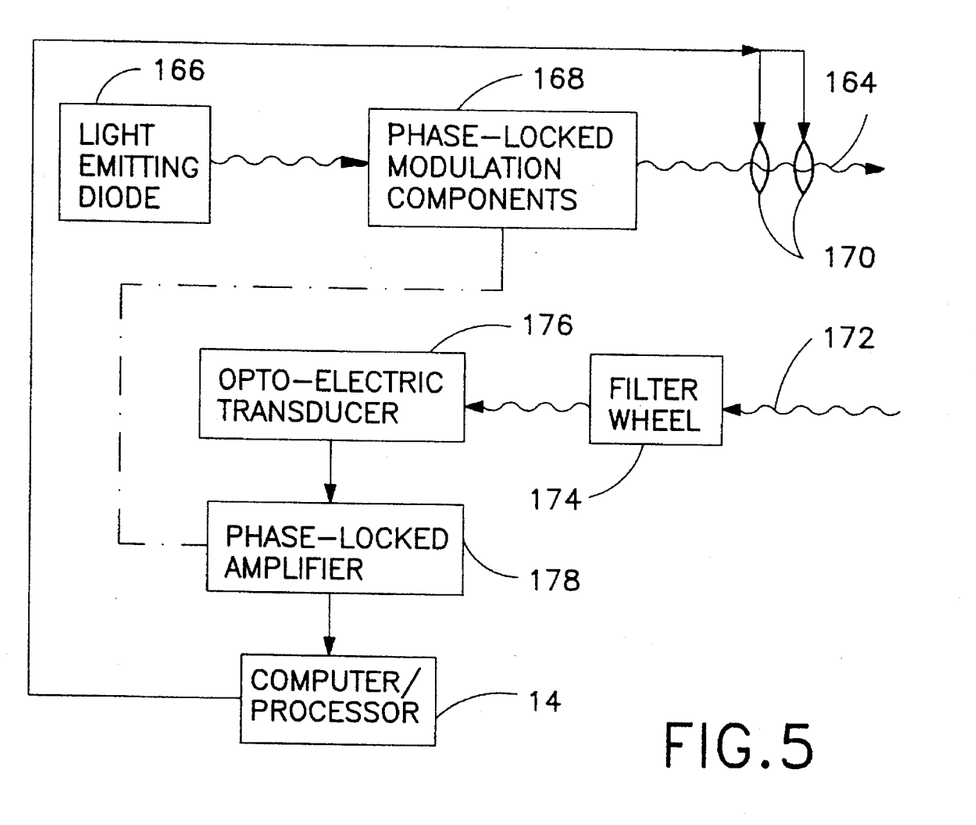
FIG. 5 is a block diagram of supplemental components includable in the system of FIG. 1, for remotely collecting data as to a subject's respiration rate.

FIG. 5 illustrates components for monitoring the differential remote absorption of the individual subject's exhalation gases, in order to determine respiration rate. Invisible electromagnetic radiation 164 from a source such as a light emitting diode (e.g., a laser diode) 166 is directed towards the subject's mouth. The diode generated radiation is modulated at a high rate with a phase-locked component 168. Focusing elements 170 may be controlled by computer 14 to adjust the target point.

Radiation 172 returning from the subject and particularly from gases at the subject's mouth are filtered via an electro-optical modulating polarization component exemplarily in the form of a filter wheel 174 rotating at a speed between 300 and 1,000 Hz. An opto-electric transducer or detector 176 senses the radiation penetrating filter wheel 174. An amplifier 178 phase-locked with modulator component 168 serves to detect signals only at the frequency of modulation. Any ambient constant energy which is not part of the measuring signal is filtered out.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for remotely determining information relating to a person's emotional state, comprising:

generating waveform energy having a predetermined frequency and a predetermined intensity, the generating of said waveform energy being implemented at a location remotely spaced from a target individual;

automatically monitoring the position of the individual;

wirelessly transmitting said waveform energy towards the individual;

detecting energy emitted from a predetermined point on the individual in response to the waveform energy;

automatically tracking the location of said point; and automatically analyzing the emitted energy to derive information relating to the individual's emotional state.

2. The method defined in claim 1 wherein said step of analyzing includes the steps of:

determining a value related to a physiological parameter taken from the group consisting of blood pressure, pulse rate, respiration rate, pupil size, and perspiration; and comparing the value with a stored reference value to identify a change in said parameter.

3. The method defined in claim 2 wherein said parameter is respiration rate and said emitted energy is reflected from the individual's chest wall, further comprising the steps of:

processing the emitted energy to determine location of the individual's chest wall; and automatically monitoring the individual's position and compensating for changes in the individual's position in determining changes location of the individual's chest wall.

4. The method defined in claim 3 wherein said waveform energy is taken from the group consisting of modulated electromagnetic radiation and pressure waves.

5. The method defined in claim 2 wherein said reference value includes a previously measured value for said parameter, further comprising the step of storing said parameter in encoded form in a memory.

6. The method defined in claim 1 wherein said waveform energy is collimated modulated electromagnetic radiation, said step of generating including the steps of:

producing an electromagnetic waveform of said predetermined frequency;

modulating said electromagnetic waveform; and collimating the modulated electromagnetic waveform, said step of transmitting including the step of directing said electromagnetic waveform to said predetermined point on said individual.

7. The method defined in claim 6, further comprising the step of processing said emitted energy to derive a measure of perspiration on the individual at a predetermined location.

8. The method defined in claim 1 wherein said step of monitoring includes the steps of deriving a contour of said individual and comparing said contour with previously determined generic contour data.

9. The method defined in claim 1 wherein said step of analyzing includes the step of measuring the emitted energy to determine at least one parameter selected from the group including frequency, amplitude or intensity, phase, and polarization, said step of analyzing also including the step of automatically comparing the determined parameter with a reference value.

10. The method defined in claim 9 wherein said reference value incorporates at least one prior measurement of the selected parameter with respect to the individual.

11. The method defined in claim 1, further comprising the step of changing a frequency of said waveform during a sequence of successive measurements.

12. A system for remotely determining information relating to a person's emotional state, comprising:

generator means for generating waveform energy having a predetermined frequency and a predetermined intensity, said generator means being remotely spaced from a target individual;

transmitter means operatively connected to said generator means for wirelessly transmitting said waveform energy towards the individual, said transmitter means including directional means for directing said waveform to a predetermined point on said individual;

detector means for detecting energy emitted from the individual in response to the waveform energy;

processing means operatively connected to said detector means for analyzing the emitted energy to derive information relating to the individual's emotional state, said processing means being operatively connected to at least one of said generator means and said transmitter means for controlling emission of energy towards the individual; and monitoring means operatively connected to said processing means for monitoring the location of the individual, said monitoring means being operatively connected to said directional means for controlling the operation thereof.

13. The system defined in claim 12 wherein said processing means includes first means for determining a value related to a physiological parameter taken from the group consisting of blood pressure, pulse rate, respiration rate, pupil size, and perspiration and second means operatively connected to said first means for comparing the determined value with a stored reference value to identify a change in said parameter.

14. The system defined in claim 13 wherein said parameter is respiration rate and said emitted energy is reflected from the individual's chest wall, said processing means including third means for processing the emitted energy to determine location of the individual's chest wall and means for automatically monitoring the individual's position and compensating for changes in the individual's position in determining changes in location of the individual's chest wall.

15. The system defined in claim 14 wherein said waveform energy is taken from the group consisting of modulated electromagnetic radiation and ultrasonic pressure waves, said generator means including at least one of means for generating electromagnetic energy and means for generating ultrasonic pressure waves.

16. The system defined in claim 13 wherein said parameter is blood pressure, said waveform energy is a first ultrasonic pressure wave and said emitted energy is a second ultrasonic pressure wave, said processing means including means for processing said second ultrasonic pressure wave to derive a rate of blood flow in a preselected blood vessel of the individual, said processing also including means for automatically calculating a blood pressure parameter from the derived blood flow rate.

17. The system defined in claim 13 wherein said parameter is pupil size, said waveform energy being electromagnetic radiation, said detector means including pixel receptors of a camera, said processing means including means for automatically counting pixels corresponding to a diameter of the individual's pupil.

18. The system defined in claim 13 wherein said reference value includes a previously measured value for said parameter, further comprising memory means for storing said parameter in encoded form.

19. The system defined in claim 12 wherein said waveform energy is collimated modulated electromagnetic radiation, said generator means including means for producing an electromagnetic waveform of said predetermined frequency and means for collimating said electromagnetic waveform.

20. The system defined in claim 19, further comprising means for processing said emitted energy to derive a measure of perspiration on the individual at a predetermined location.

21. The system defined in claim 12 wherein said monitoring means includes means for deriving a contour of said individual and means connected thereto for comparing said contour with previously determined generic contour data.

22. The system defined in claim 12 wherein said detector means includes means for measuring the emitted energy to determine at least one parameter selected from the group including frequency, amplitude or intensity, phase, and polarization, said processing means including means for comparing the determined parameter with a previously determined reference value.

23. The system defined in claim 22 wherein said reference value incorporates at least one prior measurement of the selected parameter with respect to the individual, said processing means including means for deriving said reference value from said prior measurement.

24. The system defined in claim 12 wherein said generator means includes means for changing a frequency of said waveform during a sequence of successive measurements.

25. A method for remotely determining information relating to a person's emotional state, comprising:

generating waveform energy having a predetermined frequency and a predetermined intensity, the generating of the waveform energy being implemented at a location remotely spaced from a target individual;

wirelessly transmitting said waveform energy towards the individual;

detecting energy emitted from the individual in response to the waveform energy; and automatically analyzing the emitted energy to derive information relating to the individual's emotional state, the analyzing of the emitted energy including determining a value related to pulse rate and comparing the value with a stored reference value to identify a change in pulse rate, wherein said emitted energy emanates from a predetermined point on the individual overlying or on a blood vessel, further comprising processing the emitted energy to determine (1) a change in a parameter taken from the group consisting of intensity, change in intensity, change in polarization, and fluorescence of the emitted energy and (2) amount of transdermal absorption, said waveform energy being modulated electromagnetic radiation in a suboptical range of the electromagnetic spectrum.

26. The method defined in claim 25, further comprising the steps of:

automatically measuring emitted radiation at an additional point proximate to said predetermined point to determine a level of surface moisture; and compensating for surface absorption due to surface moisture in determining said amount of transdermal absorption.

27. The method defined in claim 25, further comprising the step of automatically monitoring the individual's position and tracking consequent changes in position of said predetermined point.

28. A method for remotely determining information relating to a person's emotional state, comprising:

generating waveform energy having a predetermined frequency and a predetermined intensity, the generating of the waveform energy being implemented at a location remotely spaced from a target individual;

wirelessly transmitting said waveform energy towards the individual;

detecting energy emitted from the individual in response to the waveform energy; and automatically analyzing the emitted energy to derive information relating to the individual's emotional state, the analyzing of the emitted energy including determining a value related to blood pressure and comparing the value with a stored reference value to identify a change in blood pressure, wherein said waveform energy is a first ultrasonic pressure wave and said emitted energy is a second ultrasonic pressure wave, further comprising processing said second ultrasonic pressure wave to derive a rate of blood flow in a preselected blood vessel of the individual, the analyzing of the energy emitted from the individual including automatically calculating a blood pressure parameter from the derived blood flow rate.

29. A method for remotely determining information relating to a person's emotional state, comprising:

generating waveform energy having a predetermined frequency and a predetermined intensity, the generating of the waveform energy being implemented at a location remotely spaced from a target individual;

wirelessly transmitting said waveform energy towards the individual;

detecting energy emitted from the individual in response no the waveform energy; and automatically analyzing the emitted energy to derive information relating to the individual's emotional state, the analyzing of the emitted energy including determining a value related to a physiological parameter and comparing the value with a stored reference value to identify a change in said parameter, wherein said parameter is perspiration, said waveform energy being modulated electromagnetic radiation, the determination of surface moisture being implemented by measuring an intensity of radiation emitted from a predetermined point on the individual.

30. A system for remotely determining information relating to a person's emotional state, comprising:

generator means for generating waveform energy having a predetermined frequency and a predetermined intensity, said generator means being remotely spaced from a target individual;

transmitter means operatively connected to said generator means for wirelessly transmitting said waveform energy towards the individual;

detector means for detecting energy emitted from the individual in response to the waveform energy; and processing means operatively connected to said detector means for analyzing the emitted energy to derive information relating to the individual's emotional state, said processing means being operatively connected to at least one of said generator means and said transmitter means for controlling emission of energy towards the individual, said processing means including first means for determining a value related to pulse rate and second means operatively connected to said first means for comparing the determined value with a stored reference value to identify a change in pulse rate, wherein said emitted energy emanates from a predetermined point on the individual overlying or on a blood vessel, said first means including means for deriving (1) a change in a parameter taken from the group consisting of intensity, change in intensity, change in polarization, and fluorescence of the emitted energy and (2) amount of transdermal absorption, said waveform energy being modulated electromagnetic radiation in a suboptical range of the electromagnetic spectrum.

31. The system defined in claim 30, wherein said processing means includes means for automatically measuring emitted radiation at an additional point proximate to said predetermined point to determine a level of surface moisture and means for compensating for surface absorption due to surface moisture in determining said amount of transdermal absorption.

32. The system defined in claim 30, further comprising means operatively connected to said processing means for automatically and remotely monitoring the individual's position, thereby enabling said processing means to track changes in position of said predetermined point.

33. A system for remotely determining information relating to a person's emotional state, comprising:

generator means for generating waveform energy having a predetermined frequency and a predetermined intensity, said generator means being remotely spaced from a target individual;

transmitter means operatively connected to said generator means for wirelessly transmitting said waveform energy towards the individual;

detector means for detecting energy emitted from the individual in response to the waveform energy; and processing means operatively connected to said detector means for analyzing the emitted energy to derive information relating to the individual's emotional state, said processing means being operatively connected to at least one of said generator means and said transmitter means for controlling emission of energy towards the individual, said processing means including first means for determining a value related to perspiration and second means operatively connected to said first means for comparing the determined value with a stored reference value to identify a change in perspiration, said waveform energy being modulated electromagnetic radiation, said detector means including means for measuring an intensity of radiation emitted from a predetermined point on the individual.

* * * * *